United States Patent
Oh et al.

(10) Patent No.: US 10,481,086 B2
(45) Date of Patent: Nov. 19, 2019

(54) MASS SPECTROMETER AND SPECTROMETRY, WHICH USE NEAR INFRARED FLUORESCENCE

(71) Applicant: ASTA CO., LTD., Suwon-si, Gyeonggi-do (KR)

(72) Inventors: Jooyeon Oh, Seoul (KR); Yang Sun Kim, Seongnam-si (KR)

(73) Assignee: ASTA CO., LTD., Suwon-si, Gyeonggi-do (KR)

( * ) Notice: Subject to any disclaimer, the term of this patent is extended or adjusted under 35 U.S.C. 154(b) by 0 days.

(21) Appl. No.: 16/088,432

(22) PCT Filed: Oct. 28, 2016

(86) PCT No.: PCT/KR2016/012234
§ 371 (c)(1),
(2) Date: Sep. 25, 2018

(87) PCT Pub. No.: WO2017/171176
PCT Pub. Date: Oct. 5, 2017

(65) Prior Publication Data
US 2019/0113448 A1    Apr. 18, 2019

(30) Foreign Application Priority Data

Mar. 31, 2016    (KR) .................. 10-2016-0039480

(51) Int. Cl.
*G01N 21/359*    (2014.01)
*G01N 27/62*    (2006.01)
(Continued)

(52) U.S. Cl.
CPC .......... *G01N 21/359* (2013.01); *G01N 21/64* (2013.01); *G01N 27/62* (2013.01); *H01J 49/164* (2013.01); *H01J 49/26* (2013.01)

(58) Field of Classification Search
CPC ....... G01N 21/359; G01N 21/64; G01N 27/62
See application file for complete search history.

(56) References Cited

U.S. PATENT DOCUMENTS

| 5,469,255 A | 11/1995 | Kamada et al. |
| 6,806,464 B2 | 10/2004 | Stowers et al. |
| (Continued) | | |

FOREIGN PATENT DOCUMENTS

| JP | 06-221923 A | 8/1994 |
| JP | 10-142155 A | 5/1998 |
| (Continued) | | |

OTHER PUBLICATIONS

PCT International Search Report and Written Opinion, PCT/KR2016/012234, dated Jan. 25, 2017, 4 Pages.

*Primary Examiner* — Hugh Maupin
(74) *Attorney, Agent, or Firm* — Fenwick & West LLP

(57) ABSTRACT

A mass spectrometer using near infrared (NIR) fluorescence can comprise: a plate formed such that a sample, which includes a matrix for ionization and a fluorescent material having an excitation wavelength of an NIR wavelength band, is loaded thereon; a fluorescence detection unit formed so as to acquire a fluorescence image by using the fluorescent material from the sample on the plate; a light emission unit formed so as to emit a laser beam for ionization at the sample on the plate; and an ion detection unit formed so as to detect, by using the laser beam, ions generated from the sample. By using the NIR fluorescence, fluorescence interference due to a matrix used for MALDI imaging can be excluded even after coating the matrix, and since fluorescence interference due to auto-fluorescence inside tissue is low, fluorescence can be measured even for a thick sample.

9 Claims, 3 Drawing Sheets

(51) Int. Cl.
*G01N 21/64* (2006.01)
*H01J 49/26* (2006.01)
*H01J 49/16* (2006.01)

(56) References Cited

U.S. PATENT DOCUMENTS

| | | | |
|---|---|---|---|
| 6,937,324 B2 | 8/2005 | Kameoka | |
| 2003/0034450 A1* | 2/2003 | Karger | H01J 49/0418 250/288 |
| 2003/0184733 A1 | 10/2003 | Kameoka | |
| 2004/0075049 A1* | 4/2004 | Stowers | G01N 15/14 250/282 |
| 2005/0230615 A1* | 10/2005 | Furutani | B82Y 10/00 250/287 |
| 2006/0284078 A1* | 12/2006 | Overney | H01J 49/0418 250/288 |

FOREIGN PATENT DOCUMENTS

| | | |
|---|---|---|
| JP | 2001-091464 A | 4/2001 |
| KR | 10-2003-0077554 A | 10/2003 |
| KR | 10-2003-0078612 A | 10/2003 |
| KR | 10-0816482 | 3/2008 |
| WO | WO 02/052246 A2 | 7/2002 |
| WO | WO 2007/094525 A1 | 8/2007 |

* cited by examiner

MASS SPECTROMETER AND SPECTROMETRY, WHICH USE NEAR INFRARED FLUORESCENCE

TECHNICAL FIELD

Exemplary embodiments relate to a mass spectrometer and mass spectrometry using Near InfraRed (NIR) fluorescence, and more particularly, to a mass spectrometer and mass spectrometry based on Matrix Assisted Laser Desorption/Ionization Time of Flight (MALDI-TOF) mass spectrometry combined with NIR fluorescence imaging.

BACKGROUND ART

With the development of mass spectrometry, studies have been actively made about mass spectrometer-based diagnostics to diagnose many diseases. Among them, Matrix Assisted Laser Desorption/Ionization Time of Flight Mass Spectrometry (MALDI-TOF MS) is a method that allows for the vaporization and ionization without decomposing a sample for polymer materials, and in general, it is known as a method that can be very ideally applied to biopolymers or synthesized polymers that have large mass and are unstable to heat. Particularly, according to MALDI imaging technology that measures a mass spectrum from biological tissue and visualizes the distribution of measured compounds as an image, it is widely used in disease treatment research due to its advantage that the distribution of proteins, peptides, lipids, drugs or metabolites in the tissue can be visually identified with ease.

For MALDI imaging, a tissue boundary to measure is identified through an eye or an optical microscope, and a laser is emitted to the tissue to ionize materials in the tissue for mass spectrometry. However, in this case, it is necessary to perform mass spectrometry by emitting a laser to all parts of the tissue, and thus there is a disadvantage that it takes a long time to conduct analysis.

DISCLOSURE

Technical Problem

According to an aspect of the present disclosure, there is provided a mass spectrometer and mass spectrometry based on Matrix Assisted Laser Desorption/Ionization (MALDI) mass spectrometry combined with Near InfraRed (NIR) fluorescence imaging, thereby acquiring a precise fluorescence image without fluorescence interference by a matrix or fluorescence interference caused by auto-fluorescence in biological tissue, and through this, efficiently performing mass spectrometry.

Technical Solution

A mass spectrometer using near infrared (NIR) fluorescence according to an embodiment includes a plate on which a sample is loaded, wherein the sample includes a fluorescent material having an excitation wavelength of an NIR wavelength band and a matrix for ionization, a fluorescence detection unit is configured to acquire a fluorescence image by using the fluorescent material from the sample on the plate, a light emission unit is configured to emit a laser beam for ionization at the sample on the plate, and an ion detection unit is configured to detect, by using the laser beam, ions generated from the sample.

In an embodiment, the fluorescence detection unit is configured to acquire the fluorescence image from a first surface of the plate, and the light emission unit is configured to emit the laser beam to a second surface of the plate disposed at an opposite side to the first surface.

In an embodiment, the first surface of the plate includes an optically transparent region, and the fluorescence detection unit is further configured to acquire the fluorescence image through the optically transparent region.

The mass spectrometer according to an embodiment further includes a vacuum chamber to receive the plate, the fluorescence detection unit and the ion detection unit.

The mass spectrometer according to an embodiment further includes a moveable stage on which the plate is mounted, the moveable stage being configured moveably with respect to the fluorescence detection unit and the laser beam.

In an embodiment, the ion detection unit is further configured to calculate a mass-to-charge ratio of the ion using a time taken for the ion generated from the sample by the laser beam to reach the ion detection unit.

Mass spectrometry using NIR fluorescence according to an embodiment includes placing a sample, which includes a fluorescent material having an excitation wavelength of an NIR wavelength band and a matrix for ionization, on a plate, acquiring, by a fluorescence detection unit, a fluorescence image by using the fluorescent material from the sample on the plate, emitting, by a light emission unit, a laser beam for ionization at the sample on the plate, and detecting, by an ion detection unit, ions generated from the sample by using the laser beam.

The mass spectrometry according to an embodiment further includes, after the acquiring the fluorescence image, determining a target region to perform mass spectrometry based on the fluorescence image. Additionally, the emitting the laser beam includes emitting the laser beam to the determined target region.

In an embodiment, the emitting the laser beam to the target region includes moving the plate with respect to the laser beam by using a moveable stage on which the plate is mounted.

In an embodiment, the acquiring the fluorescence image includes acquiring the fluorescence image from a first surface of the plate. Additionally, the emitting the laser beam includes emitting the laser beam to a second surface of the plate disposed at an opposite side to the first surface.

In an embodiment, the acquiring the fluorescence image from the first surface of the plate includes acquiring the fluorescence image through an optically transparent region provided in the first surface of the plate.

The mass spectrometry according to an embodiment includes, before the acquiring the fluorescence image, placing the plate, the fluorescence detection unit, and the ion detection unit in a vacuum chamber.

The mass spectrometry according to an embodiment further includes calculating a mass-to-charge ratio of the ion using a time taken for the ion generated from the sample by the laser beam to reach the ion detection unit.

Advantageous Effects

According to the mass spectrometer and mass spectrometry using Near InfraRed (NIR) fluorescence in accordance with an aspect of the present disclosure, by using the NIR fluorescence, fluorescence can be measured even for a thick sample, and a precise fluorescence image can be acquired with a minimal interference effect caused by auto-fluorescence of other materials in the sample. Additionally, a fluorescence image of NIR wavelength band allows the measurement of a desired part of the sample without fluorescence interference by a matrix for ionization, as well as precise analysis by using NIR fluorescence imaging combined with Matrix Assisted Laser Desorption/Ionization Time of Flight (MALDI-TOF) mass spectrometry.

The mass spectrometer and mass spectrometry according to an aspect of the present disclosure has high applicability because after monitoring an animal in living state into which an NIR fluorescent material is injected, a tissue is extracted for precise analysis and it can be used in the step of analyzing again, and labeling of a target tissue or material with an NIR fluorescent material makes it possible to determine a normal tissue and an abnormal tissue that are not easy to see with an eye, and based on this, it can be used to determine a target region to perform mass spectrometry. By determining the target region in this way and performing mass spectrometry, meaning can be given to specific data from a huge amount of MALDI imaging data according to purposes, and the time required for analysis can be reduced, compared to mass spectrometry performed on the entire target tissue without prior information. Additionally, there is an advantage that a complex process of matching an optical image and a mass image acquired by separate devices is not required.

The mass spectrometer and mass spectrometry according to an aspect of the present disclosure can be usefully utilized in pharmacokinetics that is the study of kinetics of a drug in the body including absorption, distribution, metabolism and excretion, or toxicity research of a fluorescent material for clinical application of NIR fluorescence.

BEST MODE

Hereinafter, the embodiments of the present disclosure will be described in detail with reference to the accompanying drawings.

Figure 1:
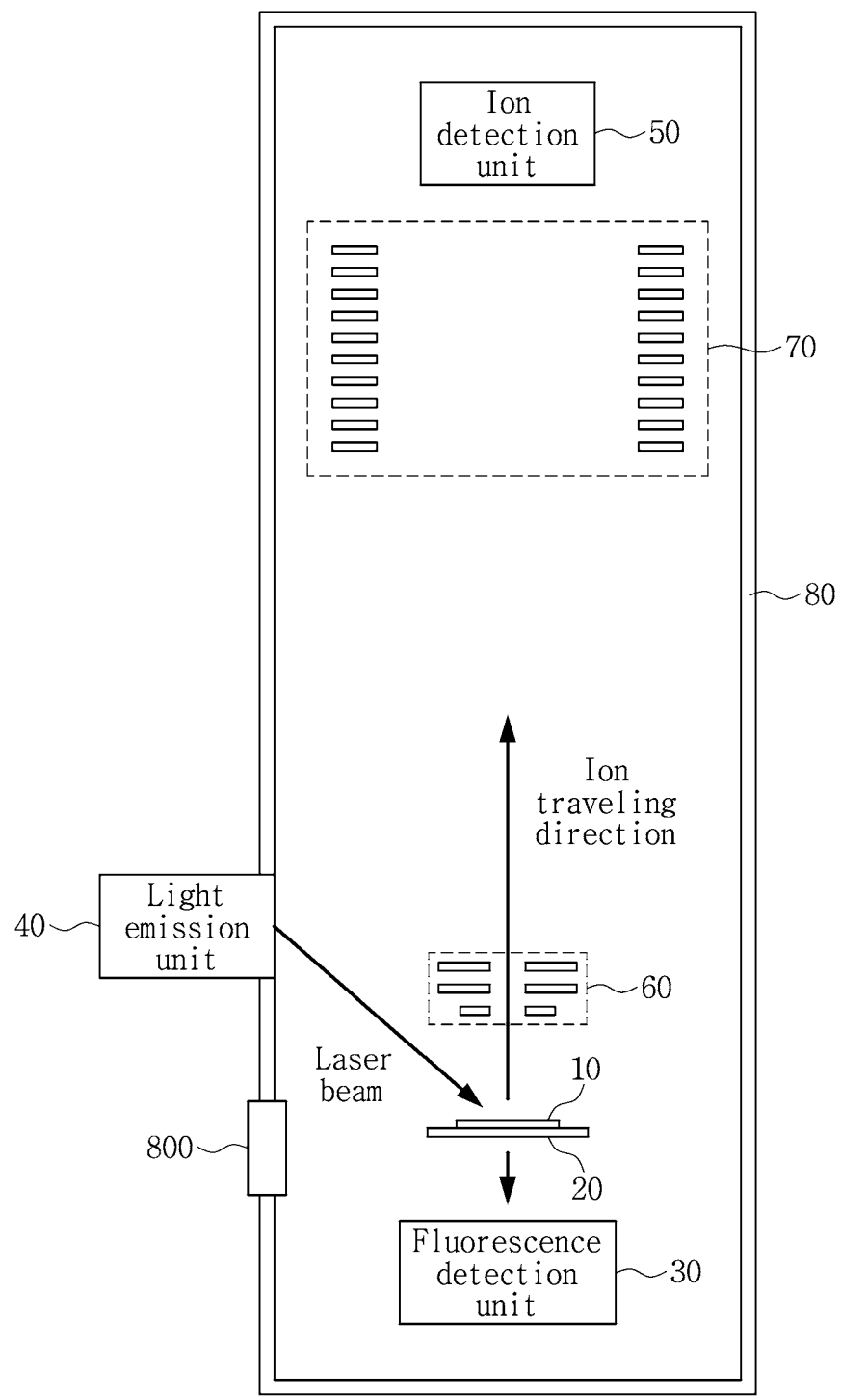
FIG. 1 is a conceptual diagram of a mass spectrometer using Near InfraRed (NIR) fluorescence according to an embodiment.

FIG. 1 is a conceptual diagram of a mass spectrometer using Near InfraRed (NIR) fluorescence according to an embodiment.

Referring to FIG. 1, the mass spectrometer according this embodiment includes a plate 10 on which a sample is loaded, a fluorescence detection unit 30 configured to take a fluorescence image of the sample loaded on the plate 10, a light emission unit 40 configured to emit a laser for ionization to the sample, and an ion detection unit 50 configured to detect ions generated from the sample to analyze the material constitution of the sample.

Each of the fluorescence detection unit 30, the light emission unit 40 and the ion detection unit 50 of the mass spectrometer according to this embodiment may have aspects of entirely hardware or partly hardware and partly software. For example, each unit 30, 40, 50 is intended to include an element for transmitting or receiving an optical signal and detecting an ion, and software for operating such an element and handling and/or processing data obtained by the element. Additionally, each unit 30, 40, 50 is not necessarily limited to one physical device, and may refer to an assembly or a collection of a plurality of components used together to fulfill an intended function.

In the embodiments of the present disclosure, a fluorescent material and a matrix for ionization are included in the sample to be loaded on the plate 10.

For example, after excising an organ of a human or an animal which a fluorescent material is injected into or ingested by, a tissue is sectioned and may be used as a sample for analysis. Specifically, a quick frozen tissue sample may be prepared with a suitable thickness for Matrix Assisted Laser Desorption/Ionization (MALDI) imaging, for example, about 10 µm or more. Subsequently, the prepared sample may be placed on the plate 10, and a matrix for ionization may be coated on the sample.

Alternatively, a sample may be prepared by fluorescence post-processing of a tissue obtained from a human or an animal. For example, a sample may be prepared by cryostatic sectioning a quick frozen tissue to a suitable thickness for MALDI imaging, placing it on the plate 10, attaching a fluorescent material to the sectioned tissue, and subsequently, coating a matrix on the tissue.

The fluorescent material as used herein refers to any material that can be attached to a biological tissue of a human or an animal and generates a fluorescence signal in response to light of excitation wavelength in the NIR wavelength band. For example, in the embodiments, the fluorescent material may include, but is not limited to, a cyanine-based dye or a methylene-based dye.

The fluorescence of NIR wavelength has an advantage that it is effective for imaging of a thick tissue. Additionally, another advantage is that in the visible range, auto-fluorescence by fluorophores such as elastin and collagen in biological tissue is strong and fluorescence interference is severe, whereas in the NIR wavelength band, interference caused by auto-fluorescence is low. In this embodiment, an NIR fluorescent material is used to minimize interference caused by auto-fluorescence that may be background noise in analyzing the biological tissue. In MALDI imaging measurement, it is not easy to measure fluorescence after coating the matrix, but the use of NIR wavelength allows for the fluorescence measurement of a desired part of the sample without fluorescence interference by the matrix. Additionally, using the NIR fluorescent material, there is no need for a process of dying the tissue again by post-processing after preparing the sample for MALDI imaging, thereby increasing the efficiency of analysis.

With NIR fluorescence imaging, distribution of drugs or distribution of metabolites or abnormal tissues caused by diseases can be observed in the entire tissue, and in this embodiment, a region of interest is determined through NIR fluorescence imaging, and through mass imaging in the region of interest, more detailed and precise information can be obtained. That is, the mass spectrometry technique according to this embodiment is a combination of NIR fluorescence imaging and a MALDI imaging system, and by this combination, there are advantages that the analysis time reduces and it is possible to simultaneously see the distribution of many materials in the region of interest, as well as to create more valuable data by two imaging in combination.

The matrix as stated herein is used in mass spectrometry technique involving ionization of the sample, and refers to a liquid or solid composition used to transfer ionization energy to the sample because of having a structure that is prone to excitation. In the embodiments, any type of matrix may be used, and the matrix may include, but is not limited to, for example, 2,5-dihydroxybenzoic acid (DHB), N,N-diisopropylethyl (DIEA) and α-cyano-4-hydroxycinnamic acid (CHCA).

The sample including the matrix and the fluorescent material may be loaded on the plate 10. The plate 10 corresponds to a substrate that provides a reaction region for pre-processing and ionization of the sample. In the mass spectrometer according to this embodiment, for the fluorescence detection unit 30 to take a fluorescence image, the plate 10 may be optically transparent in the NIR wavelength band, or may include an optically transparent region at least in part. For example, the plate 10 may be made of Indium Tin Oxide (ITO) glass, but is not limited thereto.

In an embodiment, the plate 10 is placed such that a surface, on which the prepared tissue sample is placed after the tissue sample is coated with the matrix on an ITO glass or a slide glass as a sample loading region, faces the mass spectrometer.

In an embodiment, the plate 10, the fluorescence detection unit 30 and the ion detection unit 50 are placed in a vacuum chamber 80 for precise measurement. Additionally, the vacuum chamber 80 has a door 800 through which after the sample is loaded on the plate 10, the plate 10 having the sample loaded thereon can be inserted into the vacuum chamber 80. However, this is provided for illustration purposes only, and the vacuum chamber 80 may have a different opening/closing structure other than the door 800 to place the sample in the vacuum chamber 80 for measurement and remove the measured sample.

In an embodiment, the plate 10 is disposed on a moveable stage 20 that can move along one or more axial directions. For example, the moveable stage 20 may be an XY stage that can move on the plane. The relative location of the plate 10 to the laser beam and the fluorescence detection unit 30 may be changed through the movement of the moveable stage 20. For example, for precise analysis, a target region of the sample to perform mass spectrometry may be determined based on the fluorescence image, and the moveable stage 20 may be moved to emit a laser beam to the determined target region. Its detailed description is provided with reference to FIG. 3.

The fluorescence detection unit 30 acquires a fluorescence image from the sample including the fluorescent material, loaded on the plate 10. To this end, the fluorescence detection unit 30 may include a light source to emit an excitation light of NIR wavelength band for excitation of the fluorescent material, at least one optical element to focus light from the light source onto the plate 10, and an optical receiver to detect an optical signal generated from the fluorescent material. The detailed configuration of the fluorescence detection unit 30 can be easily understood by those skilled in the art from a fluorescence microscope, and thus its detailed description is omitted herein to make the subject matter of the present disclosure definite.

The light emission unit 40 is configured to emit a laser beam to the sample on the plate 10. Because the sample includes the matrix, the matrix absorbs energy from the laser and is ionized, and other materials that constitute the sample may be indirectly ionized through an ion transfer process by the matrix material. In an embodiment, the light emission unit 40 is disposed outside the vacuum chamber. The light emission unit 40 may include a laser source and at least one optical element to focus a laser onto the plate 10, and may include, but is not limited to, for example, a solid-state Yttrium Aluminum Garnet (YAG) laser source. The detailed configuration of the light emission unit 40 can be easily understood by those skilled in the art from laser equipment, and thus its detailed description is omitted herein to make the subject matter of the present disclosure definite.

The ion detection unit 50 is spatially spaced apart a preset distance from the plate 10 at which the sample is disposed, and an electric field is applied to a space between the plate 10 and the ion detection unit 50. When ions generated from the sample are accelerated by the electric field and reach the ion detection unit 50, the ion detection unit 50 may analyze the material constitution of the sample by Matrix Assisted Laser Desorption/Ionization Time of Flight (MALDI-TOF) mass spectrometry through the time of flight of each ion.

Specifically, while ions generated from the sample are accelerated by an electric field and are moving, the ions are separated according to the mass-to-charge ratio (m/z) of each material. Accordingly, the mass-to-charge ratio of each ion may be determined using the time taken for the corresponding ion to reach the ion detection unit 50, and through this, the material constitution of a region irradiated with laser in the sample may be determined. When the above-described process is repeatedly performed by emitting a laser to each part of the sample, the material constitution of the entire area irradiated with laser may be analyzed. The material constitution may be analyzed in the form of a mass spectrum showing the mass-to-charge ratio of the ions that constitute the sample and its intensity, or may be analyzed in the form of a MALDI image visually showing the distribution of materials in the sample based on the ion detection results.

In an embodiment, the ion detection unit 50 may select only ions having the mass-to-charge ratio (m/z) in a preset range as sample ions, and generate a mass spectrum or a MALDI image. Because the NIR fluorescent material included in the sample is ionized together during mass spectrometry and can reach the ion detection unit 50, the ion detection unit 50 may limit the mass-to-charge ratio range of a detection target to exclude the fluorescent material ions.

Additionally, in an embodiment, the mass spectrometer may ease the analysis of the sample by overlapping and displaying the MALDI image based on the ions detected by the ion detection unit 50 and the fluorescence image detected by the fluorescence detection unit 30 in overlay form.

In the embodiment shown in FIG. 1, the ion detection unit 50 is disposed vertically above the plate 10 to detect the ions generated from the plate 10 that are incident onto the ion detection unit 50 directly after moving in the space to which the electric field is applied. However, in other embodiment, the ion detection unit 50 may be placed in reflector mode, and in this case, the ion detection unit 50 may be disposed at a different location in the vacuum chamber 80, not vertically above the plate 10, and may detect the ions that are reflected in the direction of the ion detection unit 50 by a deflector (not shown) disposed in the ion traveling direction.

The mass spectrometer according to an embodiment further includes an optical system 60 to accelerate the ions generated from the sample and select an ion to detect from the ions, and/or an optical system 70 to decelerate the ions in a region adjacent to the ion detection unit 50. These optical systems 60, 70 may include one or more electrostatic lenses or electrodes having holes to which an electric field is applied and through which ions pass. The configuration of the optical system for this purpose is well-known to those having ordinary skill in the technical field of the present disclosure, and thus its detailed description is omitted herein to make the subject matter of the present disclosure definite.

Figure 2:
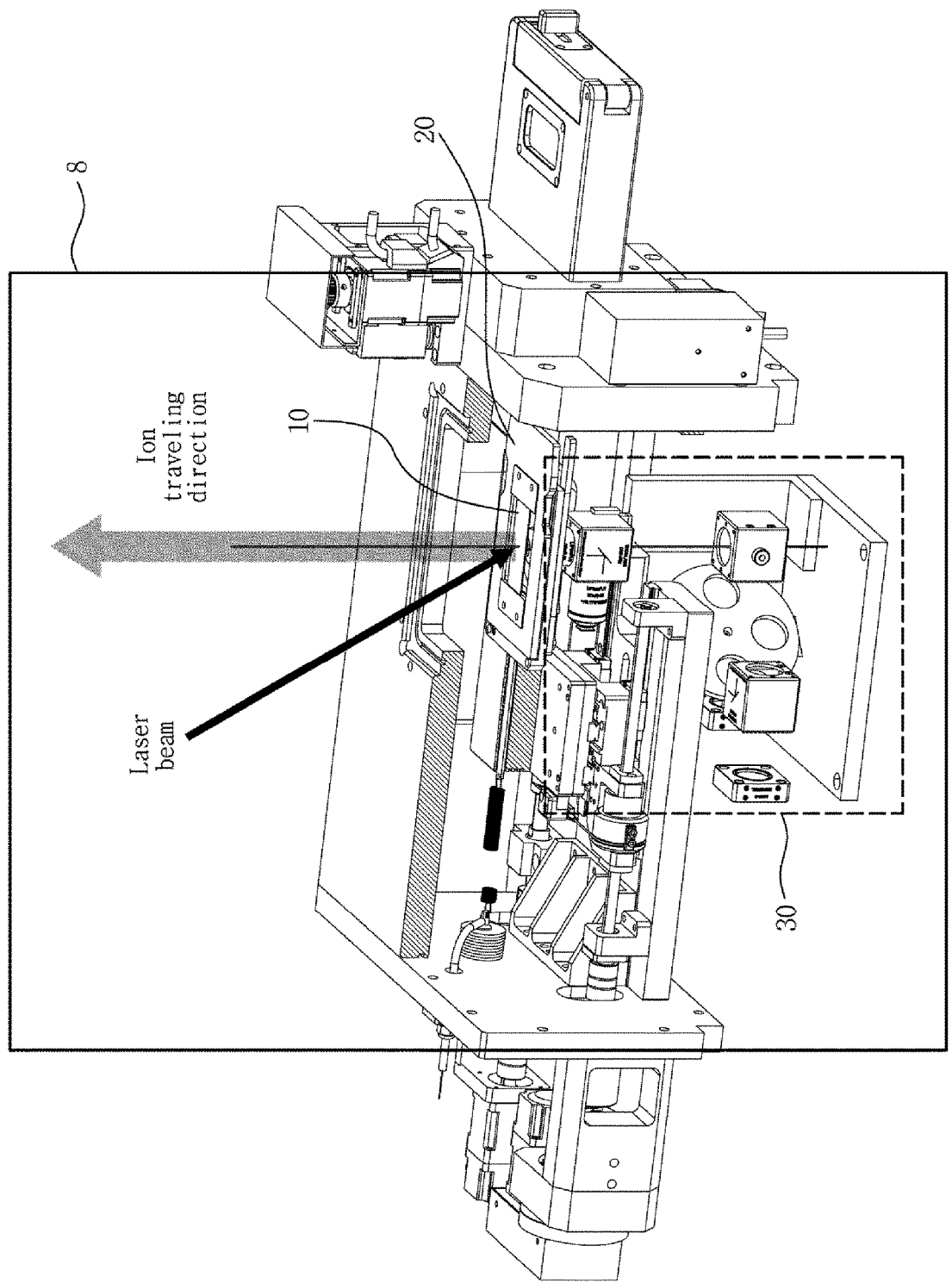
FIG. 2 is a schematic diagram of a moveable stage part on which a sample is mounted, in a mass spectrometer using NIR fluorescence according to an embodiment.

FIG. 2 is a schematic diagram of the moveable stage 20 part in the mass spectrometer using NIR fluorescence according to an embodiment.

Referring to FIG. 2, the plate 10 on which the sample is loaded, the moveable stage 20 on which the plate 10 is mounted and the fluorescence detection unit 30 are placed in the vacuum chamber. The square 8 of FIG. 2 conceptually separates a vacuum region and an atmospheric pressure region as the inside and outside of the square 8 respectively. As shown in FIG. 2, in this embodiment, the fluorescence detection unit 30 is configured to acquire the fluorescence image of the sample loaded on the plate 10 from a first surface (e.g., bottom surface) of the plate 10, and the light emission unit 40 is configured to emit a laser to a second surface (e.g., top surface) of the plate 10 to ionize the sample. In the above-described arrangement, in order to emit an excitation light from the fluorescence detection unit 30 to the sample on the plate 10 and transmit an optical signal generated by excitation of the fluorescent material from the sample to the fluorescence detection unit 30, the plate 10 and the moveable stage 20 include an optically transparent region in the NIR wavelength band at least in part.

As shown in FIG. 2, in this embodiment, by using a single stage 20, the fluorescence image may be measured in a first surface direction (e.g., downward) with respect to the plate 10 and the MALDI image may be measured by emitting a laser in a second surface direction (e.g., upward). In this way, mass spectrometry may be performed. Conventionally, even though an optical image and mass spectrometry are used together, there is a need for complex image matching between an optical image and a mass image acquired by different devices through a teaching process by an experimenter. In contrast, in this embodiment, both fluorescence image analysis and mass image analysis can be conducted on the same axis of a single stage 20, and thus there is an advantage that a separate process of matching a fluorescence image and a mass image is not required. Additionally, according to this embodiment, there is an advantage that there is no need for a separate process of putting the sample plate 10 in the vacuum chamber 80 or taking it from the vacuum chamber 80 or moving it in the vacuum chamber 80.

Figure 3:
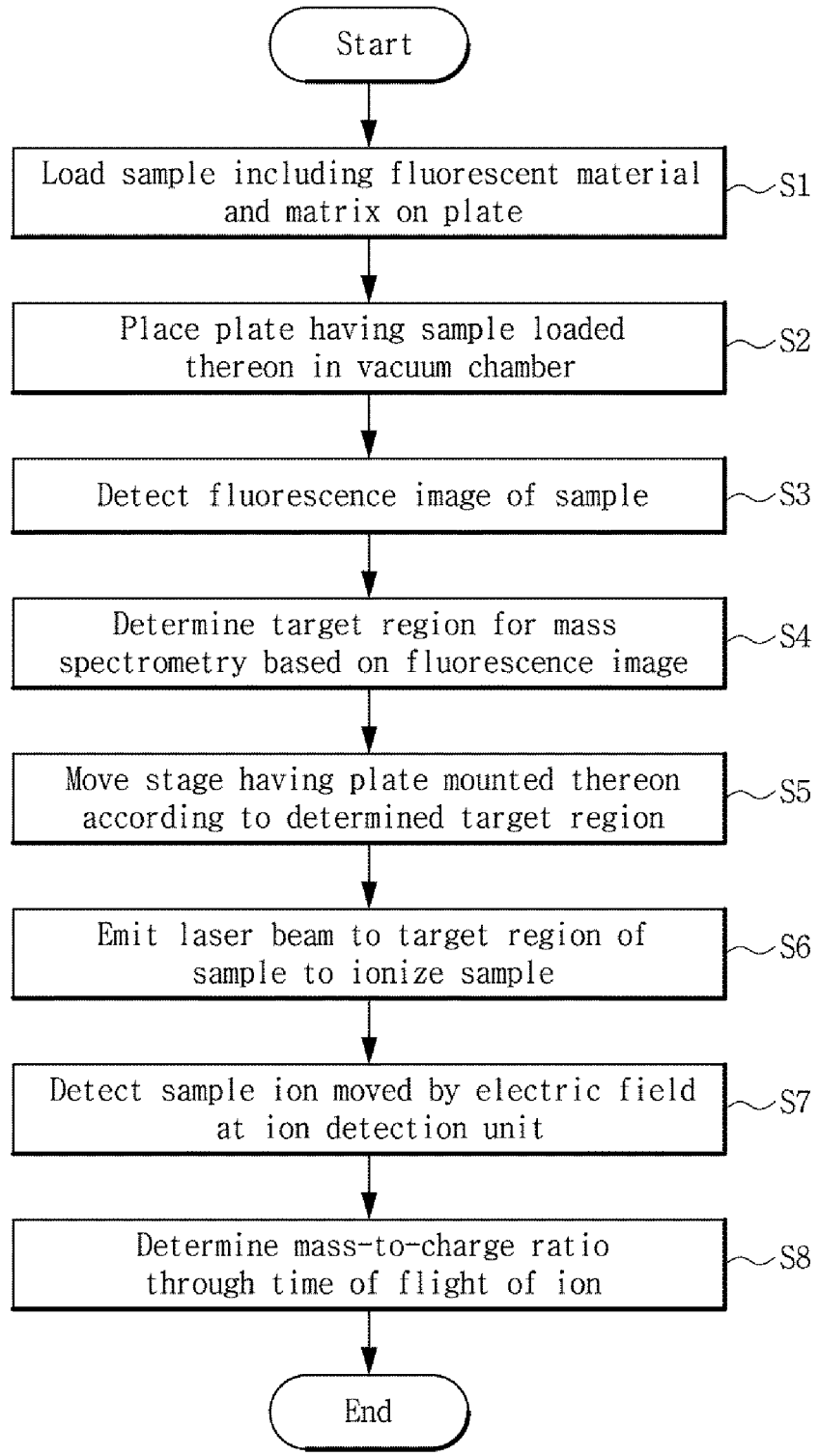
FIG. 3 is a flowchart showing each step of mass spectrometry using NIR fluorescence according to an embodiment.

FIG. 3 is a flowchart of mass spectrometry using NIR fluorescence according to an embodiment. For convenience of description, the mass spectrometry according to this embodiment is described with reference to FIGS. 1 and 3.

A mass spectrometer for performing mass spectrometry according to this embodiment is configured such that the moveable stage 20, the fluorescence detection unit 30 and the ion detection unit 50 are arranged in the vacuum chamber 80 as described above with reference to FIG. 1. In this instance, after loading a sample for analysis on the plate 10 (S1), the plate 10 may be placed on the moveable stage 20 in the vacuum chamber 80 (S2). The sample may be prepared by cryostatic sectioning a tissue of a human or an animal having already ingested a fluorescent material, placing it on the plate 10 and coating with a matrix, or by sectioned a tissue of a human or an animal in normal condition and performing fluorescent material attachment and matrix coating on the plate 10. The plate 10, on which the prepared sample is loaded, is put in the vacuum chamber 80 through the door 800 of the vacuum chamber 80.

Subsequently, a fluorescence image of the sample may be measured by the fluorescence detection unit 30 (S3). The fluorescence detection unit 30 photographs the plate 10 from the bottom of the moveable stage 20, i.e., the opposite surface to the surface of the moveable stage 20 on which the plate 10 is mounted, to acquire a fluorescence image. To enable imaging from the above-described direction, the plate 10 and the moveable stage 20 include an optically transparent region at least in part, and thus, light of excitation wavelength may be emitted to the fluorescent material through the optically transparent region and light emitted from the fluorescent material may be incident onto the fluorescence detection unit 30. Additionally, the fluorescence detection unit 30 may acquire a clear view image together with the fluorescence image.

Subsequently, a target region to perform mass spectrometry may be determined based on the fluorescence image (S4). In some cases, proteins in the biological tissue act as a disease biomarker, and when a fluorescence image is measured using a fluorescent material that specifically attaches to the disease biomarker, a region in which many disease biomarkers are distributed can be identified through a fluorescence signal. Accordingly, precise analysis of a meaningful part of interest and its boundary can be performed by the fluorescence signal, and steps related to mass imaging as described below can be performed on the part of interest. When detailed analysis by mass spectrometry is performed on the region in which many disease biomarkers are distributed and the region of interest, the time taken for analysis can be reduced compared to mass spectrometry performed on the entire tissue. For example, mass spectrometry may be performed on a region in which the fluorescence signal is found relatively strong in the fluorescence image as the target region, or mass spectrometry may be performed on the boundary of a region in which the fluorescence signal is found as the target region, and determination of the target region based on the fluorescence signal may be made in various ways according to purposes, and is not limited to a particular type. The target region may be determined by a user, or a region in which the magnitude of the fluorescence signal is equal to or larger than a preset reference value may be determined by comparing the fluorescence signal to the reference value, and based on this, the target region may be automatically determined.

When the target region to perform mass spectrometry is determined, the moveable stage 20 may be moved to place the determined target region in the range of laser beam emission (S5). After the target region of the sample is placed in the range of laser beam emission, the light emission unit 40 emits a laser to ionize the sample (S6). Because the sample includes the matrix that transfers ionization energy to the sample upon excitation by the laser, sample ions are generated from the sample by the action of the matrix.

The generated ions move by an electric field applied to a space between the plate 10 and the ion detection unit 50, and the moved ions are incident onto the ion detection unit 50 by which the ions are detected (S7). The ions are separated according to the mass-to-charge ratio (m/z) of each material while the ions are accelerated by the electric field, causing the ions to move, and the ion detection unit 50 may determine the mass-to-charge ratio of each ion using the time taken for the corresponding ion to reach the ion detection unit 50 (S8). Through the above-described process, the material constitution of the target region may be analyzed. The material constitution may be analyzed in the form of a mass spectrum showing the mass-to-charge ratio of the ions that constitute the sample and its intensity, or may be analyzed in the form of a MALDI image visually showing the distribution of materials in the sample based on the ion detection results. Additionally, the mass spectrometer may overlap the acquired MALDI image with the fluorescence image and display in overlay form.

The mass spectrometer and mass spectrometry according to the above embodiments are based on NIR fluorescence imaging and MALDI imaging in combination, and for example, after monitoring a living body in living state into which an NIR fluorescent material is injected, a tissue is taken from the living body for precise analysis and the mass spectrometer and mass spectrometry according to this embodiment can be used in the process of analyzing again, and accordingly, there is an advantage that applicability is high. In addition, conventionally, even though an optical microscope is used together with mass spectrometry, the microscope used only serves to provide an image for sketch for mass spectrometry, whereas according to this embodiment, labeling of a target tissue or material with an NIR fluorescent material makes it possible to determine a normal tissue and an abnormal tissue that are not easy to see with an eye, and based on this, a target region for mass spectrometry is determined, thereby giving meaning to specific data from a huge amount of MALDI imaging data according to purposes. Additionally, there is an advantage that a complex process of matching an optical image and a mass image acquired by separate devices is not required.

According to the mass spectrometer and mass spectrometry according to the above embodiments, by using NIR fluorescence, fluorescence can be measured even for a thick sample, and a precise fluorescence image can be acquired with a minimal interference effect caused by auto-fluorescence of other materials in the sample. Additionally, with NIR fluorescence, an advantage is that there is no need for a process of dying the sample again by post-processing after preparing the sample for MALDI imaging, thereby improving the efficiency of analysis. Further, the fluorescence image of NIR wavelength band allows for the fluorescence measurement of a desired part of the sample without fluorescence interference by a matrix material for ionization, as well as precise analysis using NIR fluorescence imaging combined with MALDI-TOF mass spectrometry. The mass spectrometer and mass spectrometry can be usefully utilized in pharmacokinetics that is the study of kinetics of a drug in the body including absorption, distribution, metabolism and excretion, or toxicity research of a fluorescent material for clinical application of NIR fluorescence.

The present disclosure has been hereinabove described with reference to the embodiments shown in the drawings, but this is provided for illustration purposes only, and those having ordinary skill in the corresponding field will appreciate that various modifications and variations may be made thereto. However, it should be noted that such modifications fall within the scope of technical protection of the present disclosure. Accordingly, the true technical protection scope of the present disclosure should be defined by the technical spirit of the appended claims.

INDUSTRIAL APPLICABILITY

Exemplary embodiments relate to a mass spectrometer and mass spectrometry using Near InfraRed (NIR) fluorescence, and more particularly, to a mass spectrometer and mass spectrometry based on Matrix Assisted Laser Desorption/Ionization Time of Flight (MALDI-TOF) mass spectrometry combined with NIR fluorescence imaging.

The invention claimed is:

1. A mass spectrometer using near infrared (NIR) fluorescence for combination of NIR fluorescence imaging and matrix assistant laser desorption/ionization (MALDI) imaging, comprising:

a plate on which a sample is loaded, wherein the sample includes a fluorescent material having an excitation wavelength of an NIR wavelength band and a matrix for ionization, the sample comprising human tissue or animal tissue and a thickness of at least 10 µm;

a fluorescence detection unit comprising a light source that irradiates the sample on the plate with excitation light to excite the fluorescent material included in the sample, the fluorescence detection unit acquiring a fluorescence image from a first surface of the plate responsive to the irradiation of the sample on the plate with the excitation light;

a light emission unit configured to emit a laser beam for ionization at the sample on the plate, the laser beam emitted to a second surface of the plate that is opposite to the first surface of the plate;

a moveable stage on which the plate is mounted, the moveable stage configured to move with respect to the fluorescence detection unit and the laser beam; and an ion detection unit configured to acquire a mass image of the sample by detecting ions generated from the sample due to the laser beam being emitted to the sample while moving the plate with respect to the laser beam using the moving stage, wherein the fluorescence detection unit and the ion detection unit are on a same axis but located opposite to each other with the plate between the fluorescence detection unit and the ion detection unit.

2. The mass spectrometer using NIR fluorescence according to claim 1, wherein the first surface of the plate includes an optically transparent region, and the fluorescence detection unit is further configured to acquire the fluorescence image through the optically transparent region.

3. The mass spectrometer using NIR fluorescence according to claim 1, further comprising:

a vacuum chamber to receive the plate, the fluorescence detection unit and the ion detection unit.

4. The mass spectrometer using NIR fluorescence according to claim 1, wherein the ion detection unit is further configured to calculate a mass-to-charge ratio of the ion using a time taken for the ion generated from the sample by the laser beam to reach the ion detection unit.

5. Mass spectrometry using near infrared (NIR) fluorescence for combination of NIR fluorescence imaging and matrix assistant laser desorption/ionization (MALDI) imaging, comprising:

placing a sample, which includes a fluorescent material having an excitation wavelength of an NIR wavelength band and a matrix for ionization, on a plate, the sample comprising human tissue or animal tissue and a thickness of at least 10 µm;

acquiring, by a fluorescence detection unit that comprises a light source that irradiates the sample on the plate with excitation light to excite the fluorescent material included in the sample, a fluorescence image from a first surface of the plate responsive to the irradiation of the sample on the plate with the excitation light;

emitting, by a light emission unit, a laser beam for ionization at the sample on the plate, the laser beam emitted to a second surface of the plate that is opposite to the first surface of the plate; and acquiring, by an ion detection unit, a mass image of the sample by detecting ions generated from the sample due to the laser beam being emitted to the sample while moving the plate with respect to the laser beam using the moving stage, wherein the fluorescence detection unit and the ion detection unit are on a same axis but located opposite to each other with the plate between the fluorescence detection unit and the ion detection unit.

6. The mass spectrometry using NIR fluorescence according to claim 5, wherein the mass spectrometry further comprises, after the acquiring the fluorescence image, determining a target region to perform mass spectrometry based on the fluorescence image, and the emitting the laser beam comprises emitting the laser beam to the determined target region.

7. The mass spectrometry using NIR fluorescence according to claim 5, wherein the acquiring the fluorescence image from the first surface of the plate comprises acquiring the fluorescence image through an optically transparent region provided in the first surface of the plate.

8. The mass spectrometer using NIR fluorescence according to claim 5, wherein the mass spectrometry comprises, before the acquiring the fluorescence image, placing the plate, the fluorescence detection unit, and the ion detection unit in a vacuum chamber.

9. The mass spectrometry using NIR fluorescence according to claim 5, wherein the mass spectrometry further comprises calculating a mass-to-charge ratio of the ion using a time taken for the ion generated from the sample by the laser beam to reach the ion detection unit.

\* \* \* \* \*